United States Patent
Sorenson et al.

(10) Patent No.: US 7,232,425 B2
(45) Date of Patent: Jun. 19, 2007

(54) APPARATUS AND METHOD FOR SPECIFIC INTERSTITIAL OR SUBCUTANEOUS DIFFUSION AND DISPERSION OF MEDICATION

(75) Inventors: James LeVoy Sorenson, Salt Lake City, UT (US); LeVoy Golden Haight, West Jordan, UT (US)

(73) Assignee: Sorenson Development, Inc., Salt Lake City, UT (US)

( * ) Notice: Subject to any disclaimer, the term of this patent is extended or adjusted under 35 U.S.C. 154(b) by 1119 days.

(21) Appl. No.: 10/080,292

(22) Filed: Feb. 21, 2002

(65) Prior Publication Data
US 2002/0123723 A1   Sep. 5, 2002

Related U.S. Application Data

(60) Provisional application No. 60/272,867, filed on Mar. 2, 2001.

(51) Int. Cl.
*A61M 5/178* (2006.01)
(52) U.S. Cl. .......................... 604/164.06; 604/164.06; 604/158
(58) Field of Classification Search ................ 604/264, 604/523, 103.01, 509, 167.04, 99.3, 48, 30, 604/500, 249, 529, 22, 101.03, 103.03, 175, 604/524, 19; 607/138, 104; 606/28, 41; 600/29
See application file for complete search history.

(56) References Cited

U.S. PATENT DOCUMENTS

| | | | |
|---|---|---|---|
| 4,168,799 A | | 9/1979 | Turner |
| 4,450,150 A | | 5/1984 | Sidman |
| 5,156,597 A | * | 10/1992 | Verreet et al. .............. 604/175 |
| 5,285,968 A | | 2/1994 | McSheehy |
| 5,299,885 A | | 4/1994 | Prassas et al. |
| 5,368,235 A | | 11/1994 | Drozdoff et al. |
| 5,374,138 A | | 12/1994 | Byles |
| 5,425,723 A | * | 6/1995 | Wang .......................... 604/523 |
| 5,437,290 A | * | 8/1995 | Bolger et al. ............... 128/898 |
| 5,474,398 A | | 12/1995 | Prassas et al. |
| 5,773,577 A | | 6/1998 | Cappello |
| 5,807,306 A | | 9/1998 | Shapland et al. |
| 5,834,001 A | | 11/1998 | Dionne et al. |
| 5,954,714 A | * | 9/1999 | Saadat et al. .................. 606/28 |
| 5,957,901 A | * | 9/1999 | Mottola et al. .............. 604/264 |
| 6,071,230 A | * | 6/2000 | Henalla ........................ 600/29 |
| 6,107,004 A | * | 8/2000 | Donadio, III ................ 430/320 |
| 6,315,789 B1 | * | 11/2001 | Cragg ......................... 606/232 |
| 6,488,662 B2 | * | 12/2002 | Sirimanne .............. 604/164.01 |

\* cited by examiner

Primary Examiner—Kevin C. Sirmons
Assistant Examiner—Elizabeth MacNeill
(74) Attorney, Agent, or Firm—TraskBritt

(57) ABSTRACT

A medication discharge assembly useful in patient systems includes a tubular element and a stylet. In a first, closed position, the stylet is seated within the tubular element and may provide a piercing point facilitating insertion of the tubular element to a treatment site. In a second, open position, the stylet is removed from the tubular element, and the tubular element provides a travel pathway for a drug introduced to the tubular element at a proximal connection port for specific interstitial and subcutaneous diffusion and dispersion of medication along the tubular element's length near a distal discharge port through disparate perforations, which may be formed as striations of increasing length nearer the distal discharge port. The stylet in the first position may be oriented to seal this travel pathway. Depth-finding features associated with the tubular element, visually perceptible and particularly useful for placement of the assembly, may be included.

22 Claims, 4 Drawing Sheets

APPARATUS AND METHOD FOR SPECIFIC INTERSTITIAL OR SUBCUTANEOUS DIFFUSION AND DISPERSION OF MEDICATION

CROSS-REFERENCE TO RELATED APPLICATIONS

Under the provisions of 35 U.S.C. § 119(e), priority is claimed from U.S. Provisional Patent Application Ser. No. 60/272,867 filed on Mar. 2, 2001.

TECHNICAL FIELD

This invention relates generally to medication infusion systems and is specifically directed to such systems for specific interstitial diffusion and dispersion of medication. It provides a particularly useful application for uniform dispersion of medication to perfuse a treatment site including a patient pain interface.

BACKGROUND

Heretofore, introduction of medication at a preferred site within the body of a patient has been accomplished through delivery structure in either of essentially two forms, namely, injection through a needle or infusion through a catheter. Each of these methodologies has resulted in delivery of medication primarily to a location immediately adjacent to the distal tip of the needle or catheter. After injection through a needle or infusion through a catheter, the medication is absorbed into, or spreads by osmosis to, the tissues immediately adjacent to the discharge orifice of the needle or catheter, or the absorption field, for localized treatment. The medication then in varying degrees migrates with the normal circulatory and other systems of the body until fully metabolized systemically.

As the migrating medication is dispersed, inefficiencies in treatment may result. Significant factors in this context include the particular medication selected and, in part due to the varying size of treatment sites causing pain, the varying number of pain receptors to be blocked from patient to patient. For example, treatment sites that require a more concentrated dosage of a given medication may receive a preferred dosage concentration for a short period of time after which, as the medication is dispersed systemically, the treatment site is supplied a dosage concentration that is lower than that preferred. The dosage concentration must be sustained at a level sufficient to maintain a concentration gradient that reduces or eliminates the pain in the treatment site so long as it is desirable to do so. In some instances, excessive doses have been utilized to compensate for this dispersion effect, inherently resulting in exposure of the treatment site to unnecessary levels of medication. Such exposure not only wastes medication that may be expensive, but may also have a detrimental impact on the surrounding tissue as well as precipitating adverse side effects in other aspects of the patient's systemic physiology.

Another challenge imposed by the foregoing dispersion conundrum involves the rate and frequency of introduction of medication to surgical and general treatment sites. Historically, when a patient has required a medical treatment, it has been necessary for the patient to travel to the facilities of the medical practitioner rendering such treatment. The logistical difficulties of scheduling and commuting have discouraged patients from maintaining an optimal treatment regime. There has been a tendency, where practicable, to increase the dosage of some injected or infused medications, whereby to compensate for less frequent visits. With the onset of the prevalence of patient home treatment systems, this inefficiency is being addressed by the use of portable, patient-operated pumps in accordance with physician-directed protocols.

A technical difficulty exists with respect to the accuracy of the placement of the medicinal delivery orifice relative to the desired treatment site. It has not always been clear how far a needle or catheter should be inserted into a body to optimize the likelihood that the discharge orifice is ideally positioned to deliver medication, within an acceptable degree of precision, to the treatment site. Use of flexible catheters allows for potential migration of the catheter to a range of subdural or intra-cavity positions that may be undesirable, increasing the desirability of a more rigid delivery structure with means for monitoring depth of insertion.

A specific problem associated with infusion drug delivery through plural port catheters (e.g., "soaker catheters") is the inherent differences in the "flow through" characteristics of each of a plurality of discharge orifices. Uniformity in the infusion rate among the plurality of discharge orifices cannot reasonably be expected Material prior art structures are presently available from such companies as I-Flow Corporation of Lake Forest, Calif., Micor, Inc. of Allison Park, Pa., Cook Medical of Denver, Colo., and Medical Profiles, Inc. of Livonia, Mich. C.R. Bard, Inc. of Murray Hill, N.J., has dealt with soaker catheter technology involving striations but has delivered medicaments to each striation through an individual lumen to achieve uniform flow rates to a plurality of discharge orifices. I-Flow, for example, has designed a Soaker™ Catheter to infuse drugs over an area that is wider than that of point-source catheters, which deliver only at a single, discrete location. The Soaker™ Catheter device is being used intraoperatively primarily for large abdominal and chest incisions to relieve postoperative pain.

Less related but instructive prior art includes U.S. Pat. Nos. 5,834,001 to Dionne et al., entitled "Methods for Making Immunoisolatory Implantable Vehicles With a Biocompatible Jacket and a Biocompatible Matrix Core"; 5,807,306 to Shapland et al. entitled "Polymer Matrix Drug Delivery Apparatus"; 5,773,577 to Cappello entitled "Products Comprising Substrates Capable of Enzymatic Crosslinking"; and 4,450,150 to Sidman entitled "Biodegradable, Implantable Drug Delivery Depots, and Method for Preparing and Using the Same." These patents teach implantable modules for gradual, time release introduction of medication as one approach to treatment of various conditions over a larger absorption field.

Similarly, remote systems instructive in concept are disclosed in U.S. Pat. Nos. 5,299,885 to Prassas et al. and its progeny 5,474,398 entitled "Stabilized Porous Pipe"; 5,374,138 to Byles entitled "Subsurface Irrigation Apparatus and Method"; 5,368,235 to Drozdoff et al. entitled "Soaker Hose Assembly"; 5,285,968 to McSheehy entitled "Water Distribution Yoke for Tree Cultivation"; and 4,168,799 to Turner entitled "Soaker Hose."

A need remains for an efficient means of introducing medication to a treatment site of a size larger than the absorption field immediately surrounding the discharge orifice of a needle or catheter. The need would be beneficially addressed, at least in part, by provision of a plurality of discharge orifices spaced and positioned relative to each other along a distal portion of a tubular element for optimal dispersion of medication across a range of proximal absorption fields. Such orifices may be beneficially structured and arranged as striations.

A further need exists for a means of ratably introducing medication in increments and at intervals tailored to the optimal demands of any given selected treatment dosage, regime and protocol. Such a means would desirably allow for the patient, relative to his or her measured condition, to influence determination of the timing and nature of such treatment.

A need also exists for a simple means of placing a therapeutic medicinal tubular element with optimal accuracy at a treatment site. A patient diffusion and perfusion system wherein the desired depth of insertion of the tubular element can be determined visually by external viewing of the tubular element itself, thereby enabling facile location of a pain site to be treated, would be desirable.

SUMMARY OF THE INVENTION

The invention may be embodied as a medical device including an infusion tubular element assembly. The assembly includes a tubular element structure, generally a catheter or cannula. The tubular element typically comprises a continuous wall that defines an elongate lumen. The lumen provides a fluid flow path along an axis. The lumen wall generally has limited flexibility, but may be fashioned from either rigid or semirigid material. Tubular elements constructed with flexible lumen walls, or portions thereof being flexible, are also within contemplation. Located along the axis are a proximal connection port, a distal end and a distal discharge portion adjacent to the distal end. The term "axis," as used in this disclosure, generally assumes that the device in question is viewed in a straight condition, although it is recognized that in practice, some portion of the device may be distorted from this precise orientation. In such case, a nonlinear axis may be defined as passing through the center of cross-sections taken transversely through the lumen.

In a preferred embodiment, the fluid flow path through the lumen is of substantially uniform inside diameter between the proximal end and the distal end. However, flow paths having nonuniform inside diameters are also within contemplation. Embodiments having the latter configuration may be structured to minimize a pressure drop in the lumen across a dispersion zone.

In the preferred embodiment, a stylet, which may be structured and arranged as a guidewire, may further be utilized in conjunction with the tubular element. The stylet typically has significant rigidity along its length and includes a leading end, a trailing end and, in general, a substantially uniform outside diameter throughout its length. The outside diameter of the stylet is smaller than the inside diameter of the lumen of the tubular element. A distal tip is formed in the leading end of the stylet, and that tip may be structured and arranged to provide a sharp point suitable for piercing soft tissue as the stylet, fully inserted within the lumen of the tubular element, is advanced with the tubular element through the soft tissue. Additionally, the stylet in this process may function as an obturator to void the fluid flow path as the tubular element is advanced.

The tubular element includes a plurality of perforations formed in its wall along the distal discharge portion of the device. The perforations are desirably structured and arranged to achieve substantially uniform volume and rate of dispersion of therapeutic fluids from the fluid flow path therethrough.

The tubular element is structured to include perforations that extend radially through the wall with respect to the axis. The perforations may, in one embodiment, be beneficially structured to be transverse but not perpendicular to the axis.

The perforations may be uniformly dispersed with respect to each other. The perforations may alternatively be formed to be of an increasingly larger diameter or breadth as their location along the distal discharge portion approaches the distal end. In yet another alternative embodiment, the perforations may be formed as striations.

For purposes of this disclosure, the term "diameter" generally is intended to denote an average measurement across a perforation, whether or not the perforation is circular in cross section. Striations may be configured essentially as slits that may remain closed until opened by pressure in a fluid forced through the lumen and discharged through the striation. Measurements of a length corresponding to a "diameter" of such striations may, therefore, best be determined while discharging a fluid. Sometimes, for convenience, the striation length may be considered as a "diameter."

The wall of the tubular element assembly may carry indicia, or markers, externally visually perceptible for indicating depth of insertion of the tubular element. Other features and advantages of the present invention will become apparent to those of skill in the art through a consideration of the ensuing description, the accompanying and the appended claims.

BRIEF DESCRIPTION OF THE DRAWINGS

While the specification concludes with claims particularly pointing out and distinctly claiming that which is regarded as the present invention, the features of the invention may be ascertained with the aid of the drawings, wherein:

BEST MODE OF THE INVENTION

Figure 1:
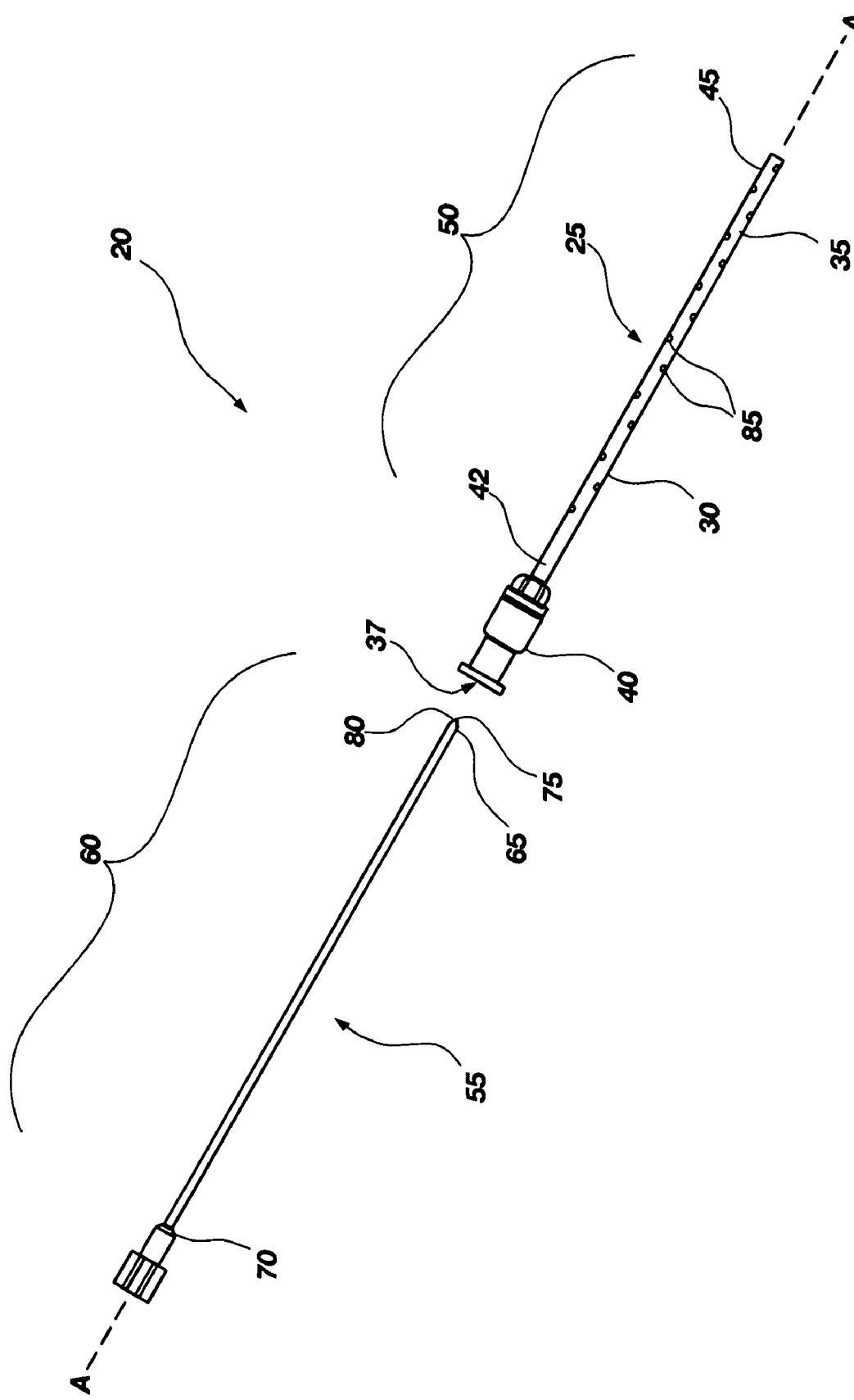
FIG. 1 illustrates an exploded side view in elevation of a tubular element and stylet assembly of this invention.

Embodiments of the present invention will be hereinafter described with reference to the accompanying drawings. It would be understood that these illustrations are not to be taken as actual views of any specific apparatus or method of the present invention, but are merely exemplary, idealized representations employed to more clearly and fully depict the present invention than might otherwise be possible. Additionally, elements and features common between the drawing figures retain the same numerical designation.

Referring to FIG. 1, an exploded side view of a preferred embodiment of a medical infusion tubular element assembly, designated generally as 20, is illustrated. The tubular element assembly 20 comprises a tubular element 25 and a stylet 55. Tubular element 25 includes a wall 30 which defines an elongate lumen 35, wherein the elongate lumen 35 includes a fluid flow path 37 extending through the tubular element 25 along axis A-A. The tubular element 25 may include a proximal connection port 40 connected to a proximal end 42 of the tubular element 25. The tubular element 25 also may include a distal discharge portion 50, which is adjacent a distal end 45 of the tubular element 25. The distal discharge portion 50 may extend any suitable predetermined length from the distal end 45 toward the proximal end 42 of the tubular element 25. The tubular element 25 may be flexible, rigid or semirigid and made of any suitable material, but preferably a polymer material.

Proximal connection port 40 may be configured for attachment to a variety of sources of pressurized treatment fluids, including but not limited to: syringes and other pressurized devices; gravity-fed sources, such as I.V. bags; tubes; and any other source of treatment fluid. Typical couplings between a fluid source and a connection port may be made with interface structure providing a friction interference fit, threaded connection, adhesive joint, or easily detachable joint structures, such as with a luer lock-type coupling.

The elongate lumen 35 may be of substantially uniform inside diameter between the proximal connection port 40 and the distal end 45. However, some configurations and circumstances may involve pressures, medicines and other variables that would benefit from a change in inside diameter between the proximal connection port 40 and the distal end 45. Such a change in diameter may encompass a gradual decrease toward the distal end 45. Step changes in diameter are within contemplation. Other changes in diameter within contemplation may be determined by a functional equation encompassing, but not limited to: injection pressure, distance traveled from the proximal connection port 40, and the number and size of upstream discharge apertures.

Figure 2:
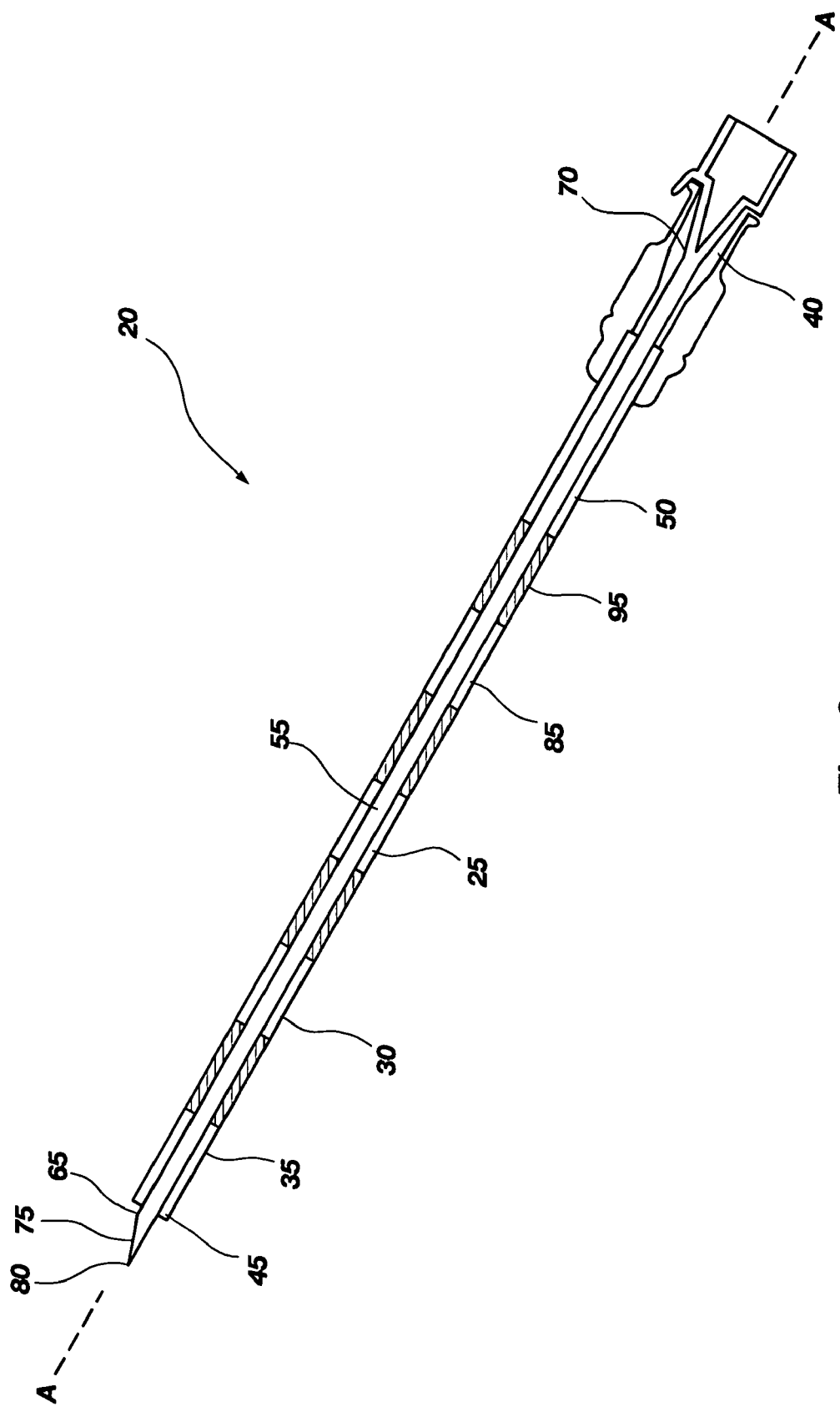
FIG. 2 illustrates a cross sectional view in elevation of the tubular element and stylet assembly of FIG. 1, in an assembled condition.

As illustrated in FIGS. 1 and 2, a rigid or semirigid stylet 55 is utilized in conjunction with the tubular element 25. The stylet 55 has a length 60 and includes a leading end 65 and a trailing end 70. Stylet 55 may be characterized having a substantially uniform outside diameter throughout its length 60 but may also include a varying outside diameter. In any case, the stylet 55 is constructed to correspond to the inside diameter of an installed tubular element 25. That is, the outside diameter of the stylet 55 is smaller than the inside diameter of the tubular element 25.

A distal tip 75 is formed in the leading end 65 of the stylet 55. Distal tip 75 may be structured and arranged to provide a sharp point 80 suitable for piercing soft tissue (not shown) as the stylet 55, fully inserted within the fluid flow path 37 along the axis A-A of the tubular element 25, is advanced with the tubular element 25 through the soft tissue. Additionally, the stylet 55 in the course of this process may be structured and arranged to function as an obturator which voids the fluid flow path along the axis A-A as the tubular element 25 is advanced.

Figure 3:
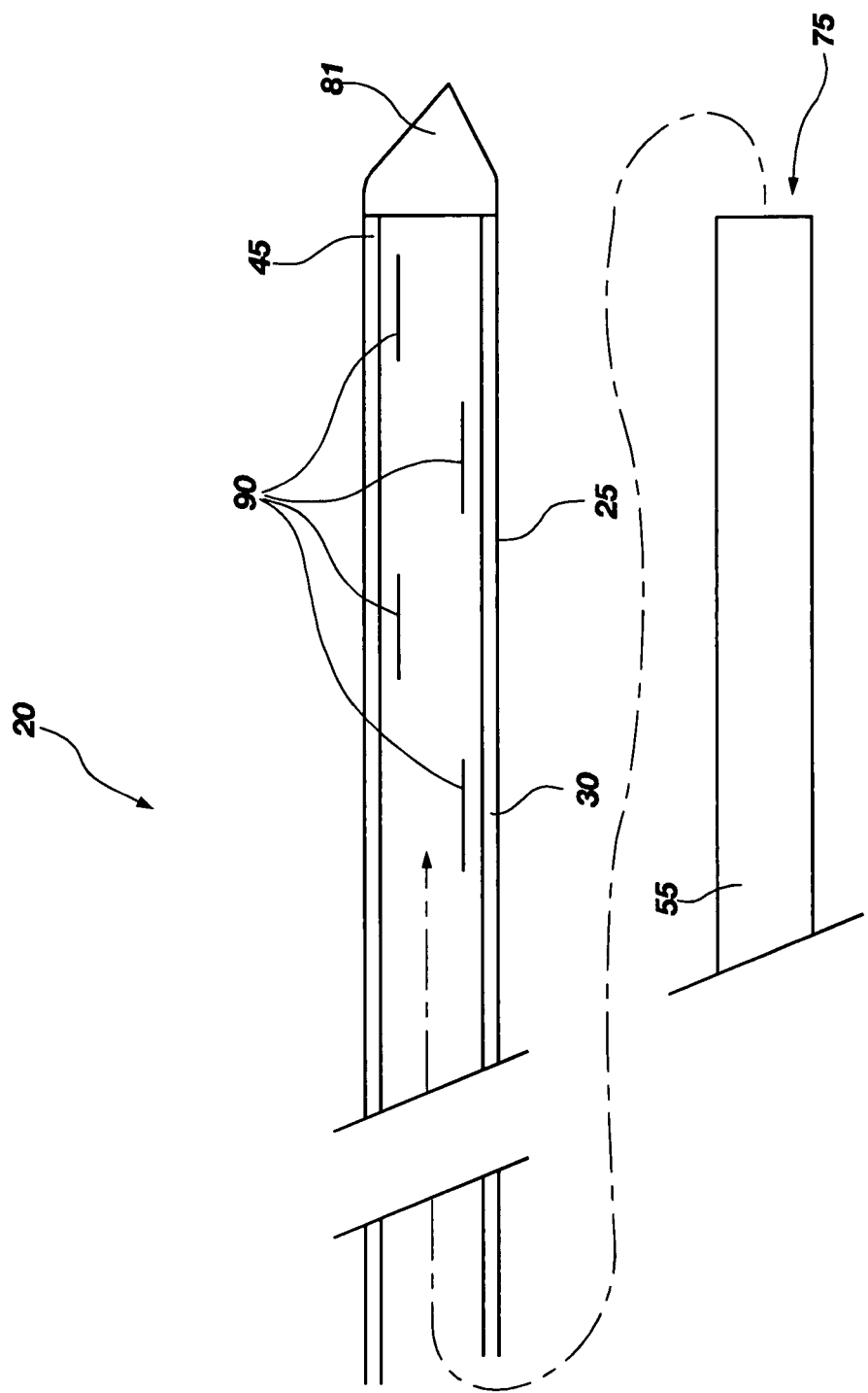
FIG. 3 is a side view in elevation of a striated tubular element and a cooperating stylus.

In an alternative embodiment, a penetrating tip 81 (FIG. 3) may be associated with the distal end 45 of tubular element 25. Such penetrating tip 81 is configured to penetrate tissue, which may include a beveled edge, a blade, a pointed tip, or serrated edge, or any combination thereof so that the penetrating tip 81 easily penetrates tissue as required. FIG. 3 illustrates striated tubular element 25 in combination with a cooperating stylus 55 having a blunt distal tip 75.

The tubular element 25 includes a plurality of perforations 85 formed through the wall 30 of the tubular element 25 along the distal discharge portion 50. The perforations 85 may be formed as striations 90, as illustrated in FIG. 3. The perforations 85 desirably are structured and arranged such that each perforation provides substantially the same flow rate for an injected treatment fluid. Such an arrangement provides substantially uniform volumetric discharge of therapeutic fluids injected through the lumen and into a treatment zone inside a patient. Such discharge more uniformly disperses medication to a treatment zone inside a patient, compared to point-source fluid introduction. Furthermore, the resulting treatment zone has a size larger than the absorption field immediately surrounding the single discharge orifice of a needle or catheter. The treatment zone for fluids injected through the instant invention may be characterized as being cylindrical, compared to the spherical treatment zone of a point-source device, such as a needle orifice.

Figure 4:
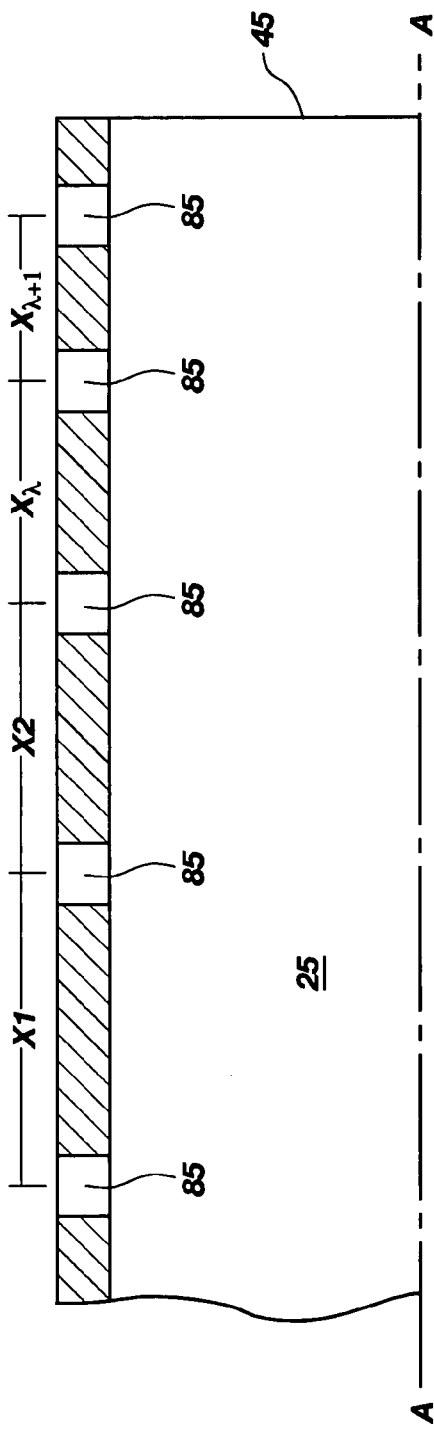
FIG. 4 is a portion of a cross-section taken in a plane passing through an axis of a tubular element.
Figure 6:
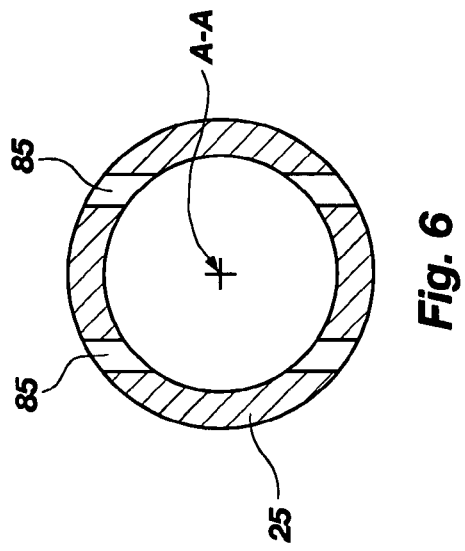
FIG. 6 is a cross-sectional view of a tubular element taken in a plane oriented perpendicular to an axis of the tube.
Figure 5:
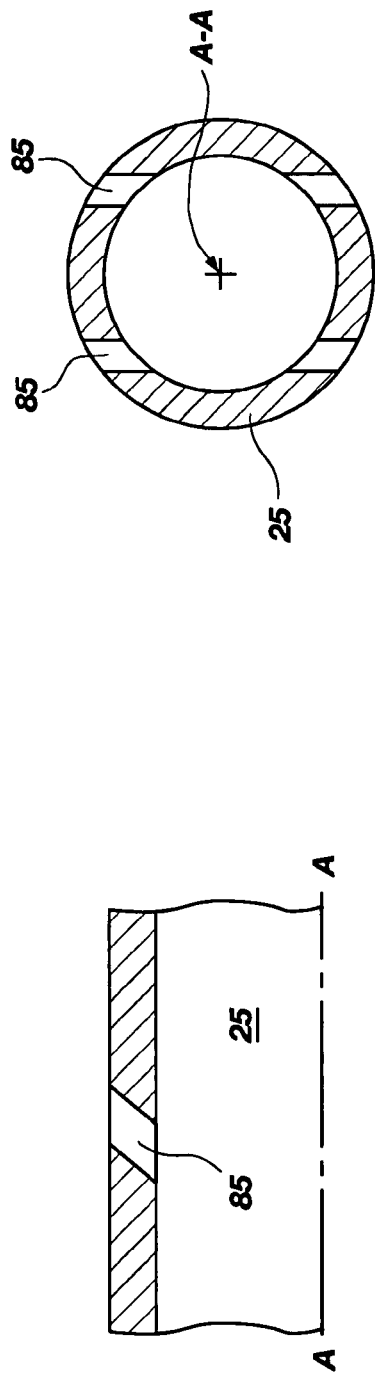
FIG. 5 is a cross-sectional view similar to the illustration of FIG. 4, but of a portion of an alternative tubular element.

With reference to FIGS. 4 through 6, the tubular element 25 may include perforations 85 that extend radially through the wall 30 with respect to the axis A-A. The perforations 85 may beneficially be structured to be transverse but not perpendicular to the axis A-A.

The perforations 85 in one embodiment may be evenly spaced apart with respect to each other. The perforations 85 may include similar size discharge openings. The perforations 85 may further be formed to include openings having an increasingly larger diameter, breadth or length to achieve greater potential throughput as their location along the distal discharge portion 50 approaches the distal end 45. In the latter case, the larger size discharge openings may help to compensate for a reduction in injection pressure at their location due to fluid discharged through upstream openings. Perforations 85 may alternatively be increasingly less spaced apart from each other by a distance Xi as their location advances from proximal end 42 to distal end 45 of the tubular element 25.

The present invention discharges treatment fluids as a substantially uniform cylindrical pool at a treatment site inside a patient. One way to characterize such fluid discharge is as follows. Discharge subzones having equal lengths may be defined in the distal discharge portion 50. Each of the subzones may have perforations 85 arranged in spacing, number, and diameter to provide a total discharge opening sized in harmony with a corresponding subzone fluid pressure. The total discharge area in each successive downstream subzone may increase to compensate for fluid discharged through upstream perforations and to maintain a substantially uniform volumetric flow rate through each of the subzones. Alternatively, or additionally, the inside diameter of the elongate lumen 35 may be adjusted to compensate for upstream pressure loss. In any event, fluids are typically discharged through orifices spaced apart along the axis of the elongate lumen 35. Such dispersion causes fluids discharged into a patient's body inherently to flow into a substantially uniform cylindrical puddle. Because the cylinder has a length along an axis, it may be oriented to more uniformly distribute a volume of treatment fluid, and to a larger area, than a corresponding fluid volume delivered as a sphere from a point-source delivery vehicle.

The wall 30 of the tubular element 25 may comprise certain indicia, such as markers 95, externally visually perceptible for indicating depth of insertion of a tubular element 25. Such markers 95 may be formed on an outside surface of the wall 30, an inside surface of the wall 30, or within the wall 30 itself and may be formed utilizing any suitable method known in the art, such as by printing.

One way to achieve relatively uniform low dispersion rates among the perforations 85 is to raise the fluid pressure in the catheter uniformly at least two PSI above the pressure of the surrounding tissue. Variables to be balanced in achieving this objective include wall thickness, material of construction, and durometer value of the tubular element 25, and length of striation 90 (or diameter of a perforation 85). A preferred embodiment for infusion of an analgesic, for example, would involve (a) a durometer in the range of fifty-five to sixty Shore A; (b) a wall thickness of approximately 0.2 millimeter in a catheter of 0.5 millimeter OD and 0.1 millimeter ID; and (c) a striation 90 length of approximately five millimeters. In this embodiment, the total distal discharge portion 50 is approximately one inch in length and the pressure within the elongate lumen 35 throughout the distal discharge portion 50 immediately prior to infusion of medication is approximately two to three PSI above the surrounding tissue. An alternative preferred embodiment for infusion of a medicament to be introduced at a higher rate to a site involving little to no movement in surrounding tissue (not illustrated), for example, may involve (a) a durometer of approximately ninety Shore A; (b) a wall thickness of approximately 0.1 millimeter in a cannula of 0.5 millimeter OD and 0.3 millimeter ID; and (c) a striation 90 length of approximately one centimeter. In this alternative embodiment, the distal discharge portion 50 is approximately two inches in length and the PSI within the elongate lumen 35 immediately prior to injection of medication is approximately four PSI above the surrounding tissue.

It has been determined, in one embodiment of the invention, that for every one-quarter inch increase in the length of the distal discharge portion 50, the PSI gradient should be increased by approximately two PSI to maintain even rates of dispersion. This may serve as a general rule-of-thumb and can operate within practical limits on available length of the distal discharge portion 50. However, the PSI gradient may be increased less where striation 90 length is greater. Similarly, where the durometer of material forming the tubular element 25 is substantially increased, wall thickness may be decreased and the length of any given individual striation 90 could be increased. It is currently preferred for a striation 90 length to generally be less than one centimeter. Striations 90 are preferably structured and arranged to be substantially parallel with the axis A-A of the tubular element 25 and radially spaced apart. In one preferred embodiment, there are not more than four striations 90 circumferentially spaced apart an approximately equal distance from one another at any given location along the axis A-A. Striations 90 are desirably separated from each other along the axis A-A at a distance sufficient to ensure structural integrity of the tubular element 25 relative to its material composition, wall thickness, application site and so forth.

Once being apprised of the invention and the disclosure herein, one of ordinary skill in the art will readily be able to make and use the invention.

While the present invention has been disclosed in terms of certain preferred embodiments and alternatives thereof, those of ordinary skill in the art will recognize and appreciate that the invention is not so limited. Additions, deletions and modifications to the disclosed embodiments may be effected without departing from the scope of the invention as claimed herein. Similarly, features from one embodiment may be combined with those of another while remaining within the scope of the invention.

What is claimed is:

1. A medical infusion assembly, comprising:
   a tubular element, having a proximal end and a distal end, comprising:
      a wall defining an elongate lumen between said proximal and distal ends;
      a proximal connection port at said proximal end; and
      a discharge portion adjacent to said distal end, said discharge portion comprising a plurality of perforations through said wall, said perforations being structured and arranged for substantially uniform discharge of therapeutic fluids therethrough; and
   a stylet, comprising:
      a body having a length, between a leading end and a trailing end, said body having an outside diameter along said length, said outside diameter being sized for reception within a corresponding inside diameter of said tubular element when said tubular element is installed on said stylet; and
      a distal tip formed in said leading end; wherein one of tubular element or the stylet has a sharpened distal end.

2. The medical infusion assembly of claim 1, wherein said perforations comprise a plurality of perforations spaced apart along an axis of said lumen.

3. The medical infusion assembly of claim 1, wherein said perforations comprise a plurality of perforations spaced apart around an axis of said lumen.

4. The medical infusion assembly of claim 1, wherein said perforations comprise a plurality of perforations spaced apart along an axis of said lumen and a plurality of perforations spaced apart around an axis of said lumen.

5. The medical infusion assembly of claim 1, wherein said perforations are constructed and arranged to provide a discharge opening sized in harmony with a corresponding diameter of said lumen to mutually compensate for fluid discharged through upstream perforations and to maintain a substantially uniform volumetric flow rate through each of said perforations.

6. The medical infusion assembly of claim 1, wherein said perforations each have substantially the same diameter and are spaced apart from each other by a lesser distance as perforation location approaches said distal end.

7. The medical infusion assembly of claim 1, further comprising discharge subzones of equal length being definable in said discharge portion, each of said discharge subzones having perforations arranged in spacing, number, and diameter to provide a total discharge opening sized in harmony with a corresponding subzone pressure to mutually compensate for fluid discharged through upstream subzones and to maintain a substantially uniform volumetric flow rate through each of said discharge subzones.

8. The medical infusion assembly of claim 1, wherein said discharge portion is constructed and arranged to provide a substantially uniform cylindrical discharge of fluid.

9. The medical infusion assembly of claim 1, wherein said distal tip is structured and arranged to provide a sharp point.

10. The medical infusion assembly of claim 1, wherein said distal tip comprises a blunt end, and said tubular element further comprises a penetrating tip at said distal end thereof.

11. The medical infusion assembly of claim 1, wherein said tubular element has a fluid flow path of substantially uniform inside diameter between said proximal end and said distal end.

12. The medical infusion assembly of claim 2, wherein said perforations extend radially through said wall with respect to said axis.

13. The medical infusion assembly of claim 1, wherein said perforations are transverse to, and not perpendicular to, an axis of said lumen.

14. The medical infusion assembly of claim 1, wherein said perforations are substantially uniformly dispersed with respect to each other.

15. The medical infusion assembly of claim 1, wherein said wall comprises indicia thereon externally visually perceptible for indicating depth of insertion of said tubular element.

16. The medical infusion assembly of claim 1, wherein said perforations comprise striations.

17. An infusion device, comprising:
   a tubular element having a proximal end and a distal end;
   a wall defining an elongate lumen between said proximal and distal ends;
   a proximal connection port at said proximal end; and
   a discharge portion adjacent to said distal end, said discharge portion being configured and arranged to dispense treatment fluids in a substantially uniform cylindrical pool at a treatment site in a patient,
   wherein said discharge portion comprises a plurality of spaced-apart perforations through said wall, and wherein said discharge portion has an outside diameter of about one-half millimeter; wherein the tubular element has a sharpened distal end.

18. The infusion device of claim 17, wherein said discharge portion has a length greater than about one centimeter.

19. The infusion device of claim 18, wherein said tubular element is constructed of material having a Shore A hardness of between about 50 and 100.

20. The infusion device of claim 19, wherein said tubular element comprises indicia thereon to indicate depth of insertion of said tubular element.

21. The infusion device of claim 20, in combination with an insertion stylet.

22. The infusion device of claim 20, in combination with a patient-operated fluid delivery mechanism.

* * * * *